(12) United States Patent
Sepetka et al.

(10) Patent No.: US 10,617,544 B2
(45) Date of Patent: Apr. 14, 2020

(54) IMPLANT RETENTION, DETACHMENT, AND DELIVERY SYSTEM

(71) Applicant: MicroVention, Inc., Tustin, CA (US)

(72) Inventors: Ivan Sepetka, Los Altos, CA (US); Cathy Lei, Chino Hills, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 485 days.

(21) Appl. No.: 15/268,271

(22) Filed: Sep. 16, 2016

(65) Prior Publication Data

US 2017/0079817 A1   Mar. 23, 2017

Related U.S. Application Data

(60) Provisional application No. 62/222,063, filed on Sep. 22, 2015, provisional application No. 62/220,905, filed on Sep. 18, 2015.

(51) Int. Cl.
| | |
|---|---|
| *A61F 2/95* | (2013.01) |
| *A61F 2/844* | (2013.01) |
| *A61F 2/88* | (2006.01) |
| *A61F 2/966* | (2013.01) |
| *A61F 2/90* | (2013.01) |

(Continued)

(52) U.S. Cl.
CPC .............. *A61F 2/95* (2013.01); *A61F 2/844* (2013.01); *A61F 2/88* (2013.01); *A61F 2/966* (2013.01); *A61F 2/90* (2013.01); *A61F 2002/068* (2013.01); *A61F 2002/8486* (2013.01); *A61F 2002/9505* (2013.01); *A61F 2002/9511* (2013.01); *A61F 2002/9534* (2013.01); *A61F 2002/9665* (2013.01); *A61F 2210/0076* (2013.01); *A61F 2230/0067* (2013.01)

(58) Field of Classification Search
CPC .... A61F 2/95; A61F 2/844; A61F 2/88; A61F 2002/9511; A61F 2002/9505; A61F 2002/9522; A61F 2002/9534; A61F 2/966; A61F 2/962; A61F 2002/9664; A61F 2002/8486; A61F 2002/068; A61F 2230/0067; A62F 2002/9528
See application file for complete search history.

(56) References Cited

U.S. PATENT DOCUMENTS

| | | | | |
|---|---|---|---|---|
| 6,830,575 B2 * | 12/2004 | Stenzel | ..................... | A61F 2/95 606/108 |
| 7,632,298 B2 * | 12/2009 | Hijlkema | ................. | A61F 2/95 606/194 |

(Continued)

FOREIGN PATENT DOCUMENTS

EP        2813195 A1     12/2014

OTHER PUBLICATIONS

WIPO, U.S. International Search Authority, International Search Report and Written Opinion dated Dec. 2, 2016 in International Patent Application No. PCT/US2016/052299, 11 pages.

(Continued)

*Primary Examiner* — Ashley L Fishback
(74) *Attorney, Agent, or Firm* — Inskeep IP Group, Inc.

(57) ABSTRACT

A medical implant delivery system is described. The system can be used to deliver a variety of implants including stents and/or stent grafts. The delivery system retains the implant during delivery and detaches the implant at a target location.

20 Claims, 8 Drawing Sheets

(51) Int. Cl.
*A61F 2/06* (2013.01)
*A61F 2/848* (2013.01)

(56) References Cited

U.S. PATENT DOCUMENTS

| | | | |
|---|---|---|---|
| 8,317,859 B2* | 11/2012 | Snow | A61F 2/95 623/6.12 |
| 8,986,362 B2* | 3/2015 | Snow | A61F 2/95 606/108 |
| 2006/0089703 A1 | 4/2006 | Escamilla et al. | |
| 2007/0270932 A1 | 11/2007 | Headley et al. | |
| 2008/0300667 A1 | 12/2008 | Hebert et al. | |
| 2009/0192588 A1* | 7/2009 | Shin | A61F 2/04 623/1.15 |
| 2009/0234428 A1* | 9/2009 | Snow | A61F 2/95 623/1.11 |
| 2011/0196472 A1 | 8/2011 | Sugimoto et al. | |
| 2013/0245745 A1* | 9/2013 | Vong | A61F 2/885 623/1.12 |
| 2013/0247545 A1 | 9/2013 | Solbrig et al. | |

OTHER PUBLICATIONS

European Patent Office, Extended European Search Report dated Mar. 15, 2019 in European Patent Application No. 16847470.8, 8 pages.

\* cited by examiner

IMPLANT RETENTION, DETACHMENT, AND DELIVERY SYSTEM

RELATED APPLICATIONS

This application claims benefit of U.S. Provisional Application Ser. No. 62/220,905 filed Sep. 18, 2015 entitled Implant Retention, Detachment, and Delivery System, and of U.S. Provisional Application Ser. No. 62/222,063 filed Sep. 22, 2015 entitled Implant Retention, Detachment, and Delivery System, both of which are hereby incorporated herein by reference in their entireties.

BACKGROUND OF THE INVENTION

Medical implants such as stents are sometimes used to open blood vessels to mitigate the effects of plaque buildup, to prevent embolic material within an aneurysm from escaping, as a flow diverter to limit blood flow to certain regions, or for other reasons. These implants can be delivered via an implant delivery system in which an elongated pusher is used to push the implant through a catheter or sheath to a treatment site.

Delivering implants such as stents can be a challenge since many delivery systems do not allow the implant to be repositioned after its initial deployment. Therefore, if the implant is initially deployed to an undesirable location, the physician is without recourse to adjust the implant's deployed position. Hence, there is a need for an implant delivery system that provides repositionability of an implant, as well as a reliable release structure to deploy the implant.

SUMMARY OF THE INVENTION

An implant delivery system is described. The implant delivery system can be used for a stent, stent-graft, embolic coils, plugs, occluders, or other implants.

In one embodiment, an implant delivery system comprises an implant and a retention structure.

In another embodiment, an implant delivery system comprises an implant and a retention structure. The retention structure is disposed on a distal portion of an elongated pusher and is composed of a mesh or a looped structure.

In another embodiment, an implant delivery system comprises an implant and a retention structure. The implant is affixed to said retention structure.

In another embodiment, an implant delivery system comprises an implant and a retention structure. The retention structure includes elements to grip the implant.

In another embodiment, an implant delivery system comprises an implant and a retention structure in which the retention structure separates from the implant and remains with the delivery system after the implant after the implant is detached from the delivery system.

In another embodiment, an implant delivery system comprises an implant, retention structure, and one or more tethers.

In another embodiment, an implant delivery system comprises an elongated pusher member having a retention structure disposed on a distal portion of the pusher member and engaged with an implant. The pusher, retention structure, and implant are disposed within a catheter or sheath and can be advanced out of a distal end of the catheter. The retention structure can be a conical mesh that is positioned around a proximal end of the implant. The retention structure can also be a plurality of loops disposed around a proximal end of the implant or positioned through loops on the implant. The implant may be further connected to the pusher via one or more tethers that can be broken via a mechanism located at least partially within the pusher.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

U.S. Pat. Nos. 8,182,506, 8,192,480, 8,460,332; and U.S. Pub. Nos. US20060200192, US20090062812, US20090163780, US20100268204, US20110301686, US20150289879, are hereby incorporated by reference in their entireties. These references disclose implant detachment systems that can be used in conjunction with the implant delivery system embodiments described herein. These references generally disclose a thermal detachment system in which a tether connects to an implant and is selectively broken by activating a heater coil to cause implant deployment.

The present invention is generally directed to an implant delivery system having an implant retention structure that can improve deployment of an implant, as well as retrieve an implant that has not been fully deployed. The implant retention structures of the present invention are particularly useful for deploying and repositioning stents, such as those shown in FIGS. 1 and 2, and described in greater detail below.

Figure 1:
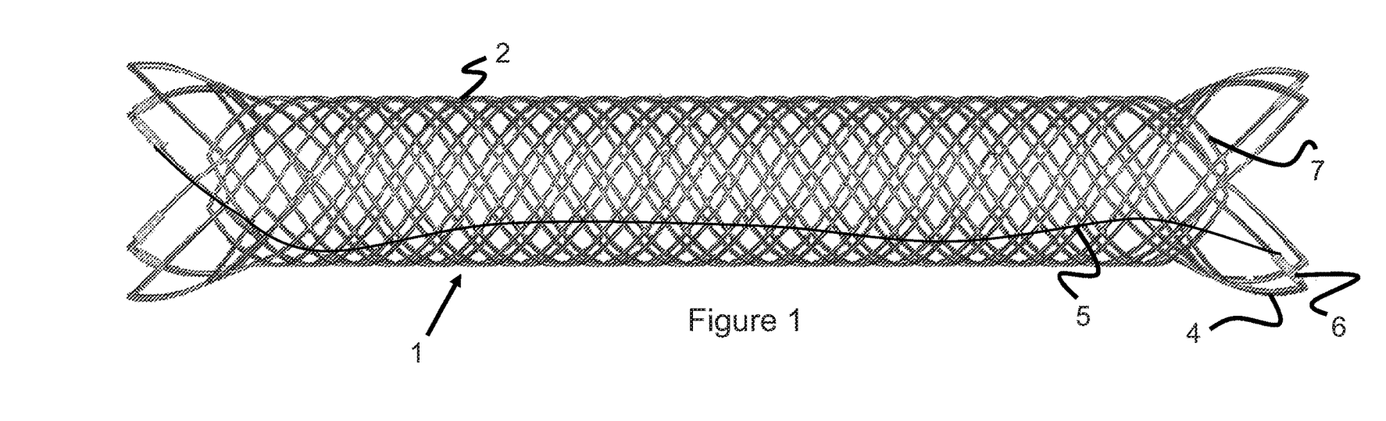
FIG. 1 illustrates an example embodiment of a woven stent that can be used with the delivery system of the present invention.

FIG. 1 illustrates a stent 1 that is woven or braided together from one or more wires 2 to form a generally cylindrical shape with a plurality of loops 4 around the perimeter of both ends of the stent 1. The ends of the wires 2 can be connected to each other via welding, bonding agents, or a similar adhesive mechanism. Once the ends are welded or bonded, the wire 2 has no "free" ends.

Each of the loops 4 may contain one or more coil members 6. Preferably, the coil members 6 are disposed around the wire 2 of the loops 4 and are composed of radiopaque material to indicate the proximal and distal ends of the stent 1. Additionally, these coil members 6 may provide additional anchoring force within a delivery device, as described in greater detail below.

In one example, a distal end of the stent 1 includes at least two loops 4 with two coil members 6 each and a proximal end of the stent 1 includes at least two loops 4 with one coil member 16 each. However, it should be understood that the stent 1 can include any number of coil members 6 on any number of loops 4.

Preferably, these coil members 6 are positioned near a center area of the loop 4, such that when the stent 1 is in a collapsed state, the coil members 6 are positioned near the very distal or very proximal end of the stent 1.

Preferably, each coil member 6 is composed of a tantalum wire 5 wound around a portion of the loop 4. Each coil member 6 can be composed of a discrete tantalum wire 5 or a single tantalum wire 5 can form multiple coil members 6 (as seen in FIG. 1). As seen in FIG. 1, the wire 5 can connect to coil members 6 on each end of the stent 100 by being located within the inner portion or lumen of the stent 1. Alternately, the wire 5 may be woven into the wires 2 of the stent 1.

One specific technique for minimizing the exposure of the distal coils 6 during retraction is to weave the stent 1 such that portions of the wire 2 overlap (i.e., are positioned at a greater outer diameter position) than the side of the loop 4 with coil 6. Some smaller, minor loops 7 are woven to overlap a first side of the loop 4 that includes the coil 6 while other minor loops 7 are woven underneath a second side of the loop 4.

Figure 2:
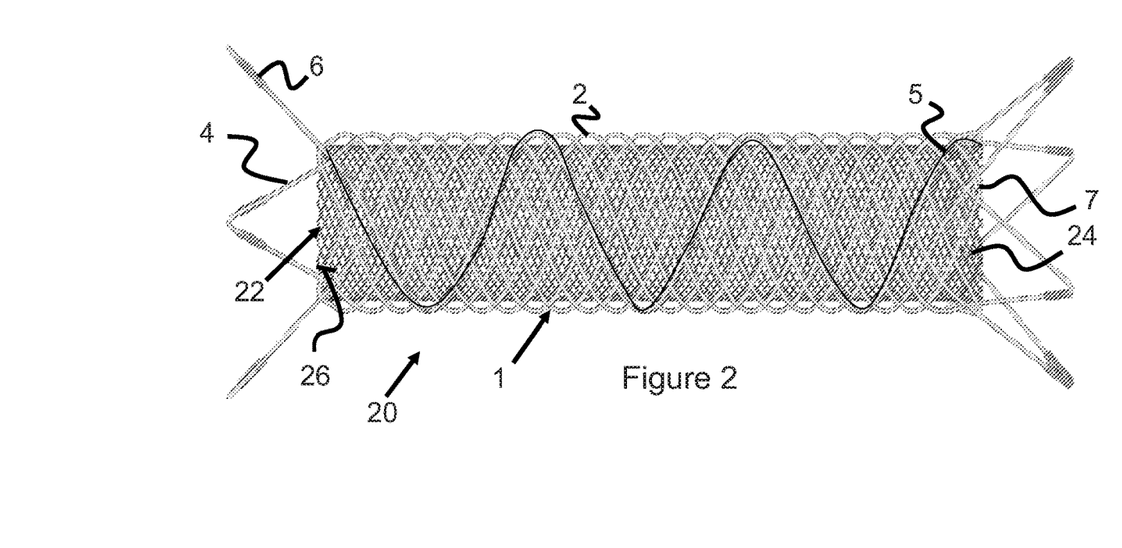
FIG. 2 illustrates an example embodiment of a woven, dual-layer stent that can be used with the delivery system of the present invention.

FIG. 2 illustrates a preferred embodiment of a dual layer stent 20 according to the present invention. Generally, the dual layer stent 20 includes an outer anchoring stent 1 that is similar to the previously described stent 1 seen in FIG. 1. The dual layer stent 20 also includes an inner flow-diverting layer 22 that is disposed within the inner lumen or passage of the anchoring stent 1. The inner flow-diverting layer 22 is preferably made from a wire 24 to form a mesh type structure.

The proximal end of the dual layer stent 20 includes a plurality of attachment members 26 that connect the anchoring stent 1 with the flow-diverting layer 22. The attachment members 26 can be composed of tantalum wire (in this case is 0.001" dia.) and can be attached to portions of wire 2 and wire 24. In another embodiment, the proximal end of the flow-diverting layer 22 can be crimped on to the wires 2 of the anchoring stent 1. In another embodiment, portions of the stent 1 and flow-diverting layer 22 can be woven through each other for attachment purposes.

Additional details of each stent 1 and 20 can be found in U.S. Pub. No. 2013/0245745, which is hereby incorporated herein by reference in its entirety.

Figure 3:
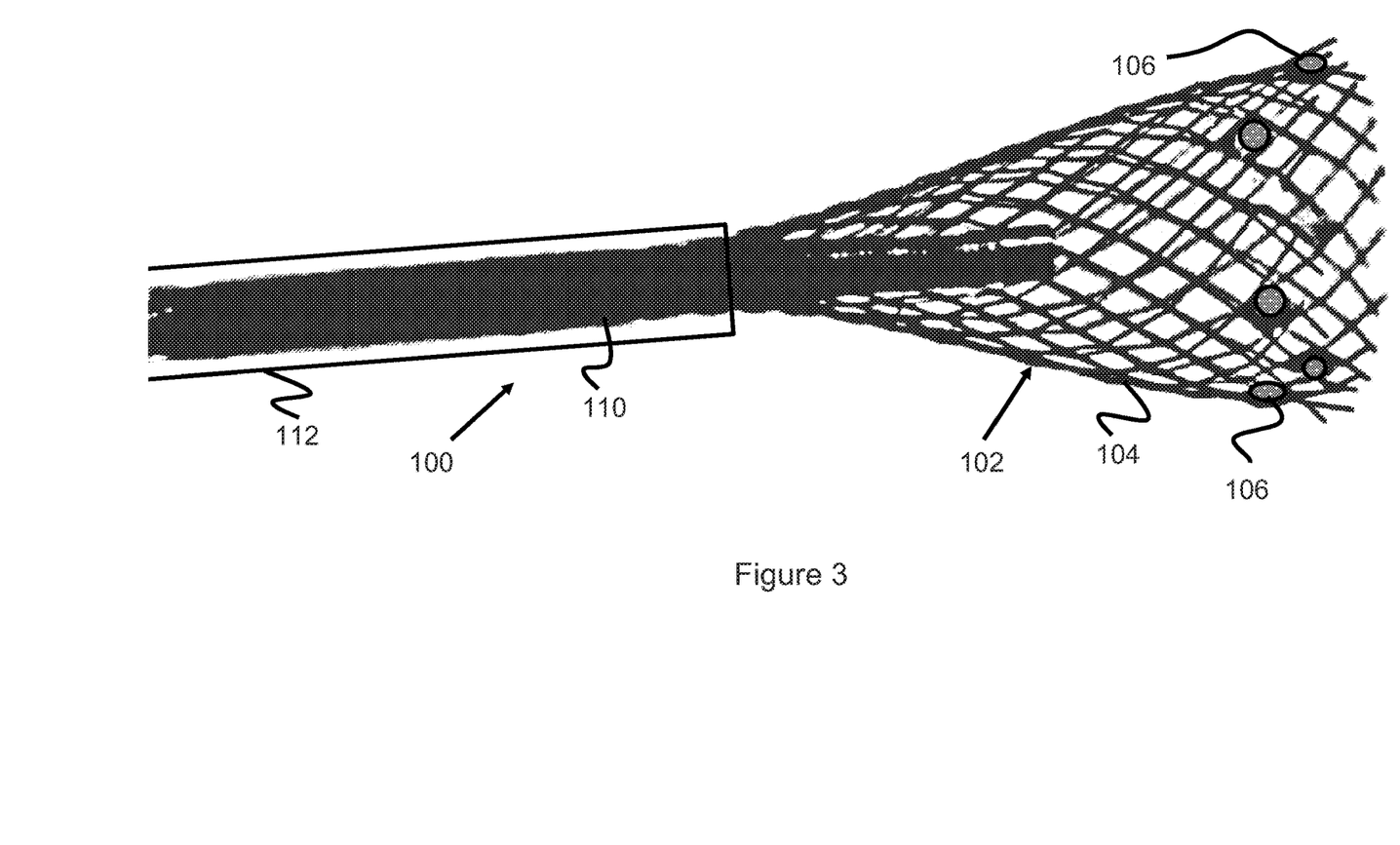
FIG. 3 illustrates a side view of an embodiment of a delivery system with a mesh or woven retaining structure.

FIG. 3 illustrates one embodiment of an implant delivery system 100 having an elongated pusher 110 and a retention structure 102 that extends from a distal portion of the pusher 110. The pusher 110, the retention structure 102, and the stent 1 (or alternately another implant device) are positioned within a catheter 112 such that at least a portion of the retention structure 102 overlaps a proximal portion of the stent 1. The catheter 112 prevents the retention structure 102 and stent 1 from expanding from their radially compressed configuration prior to deployment.

Figure 4:
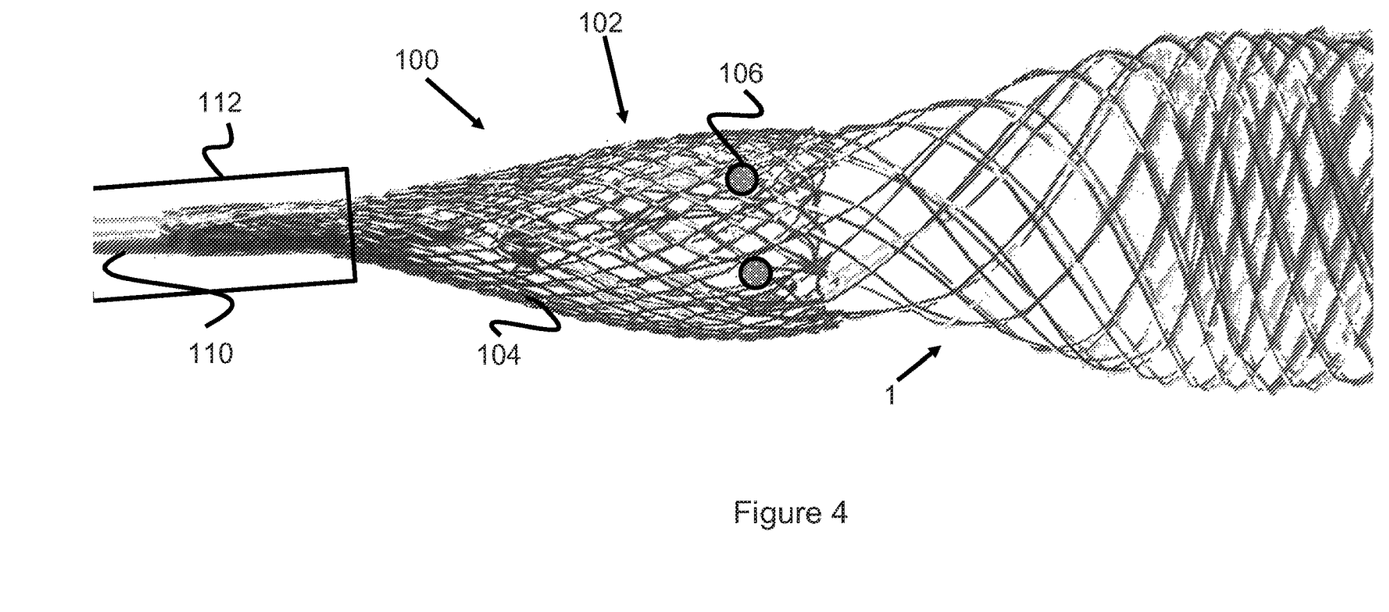
FIGS. 4 and 5 illustrate side views of the delivery system of FIG. 3 in various states of deployment.
Figure 5:
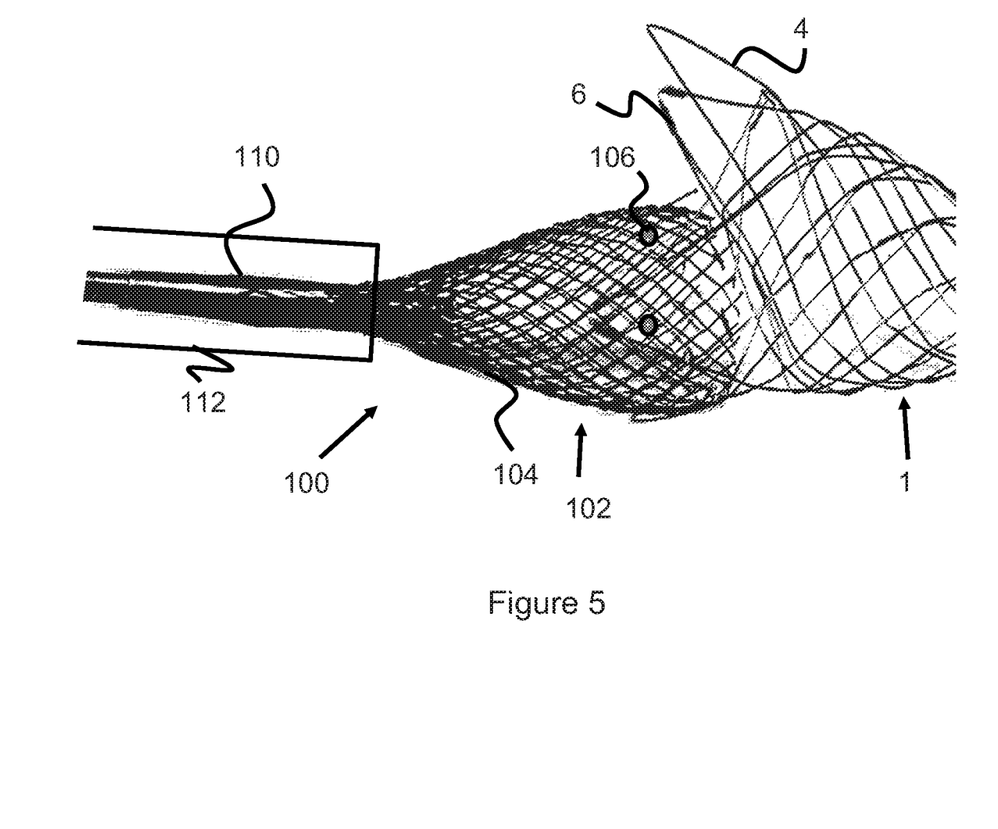

Referring to FIGS. 4 and 5, as the pusher 110 is advanced towards a distal end of the catheter 112, the retention structure 102 distally opens into a conical shape, thereby allowing the stent 1 to similarly open. If the location of the stent 1 inside the patient is undesirable, the pusher 110 and the attached retention structure 102 can be proximately withdrawn back into the catheter 112, causing the stent 1 to similarly be compressed and withdrawn back into the catheter 112 for repositioning and redeployment. The retention structure 102 allows for retraction of the stent 1 even after the stent 1 is completely outside the catheter 112. This is important because until the stent 1 is completely outside the catheter 112, the exact position of the stent 1 and the true length of stent 1 after foreshortening is not known. The retention structure 102 allows for greater opportunity for exact placement of the stent 1, since the physician will have a more opportunity to reset the stent 1 to the desired location if the initial deployment of the stent 1 is not ideal.

In one embodiment, the retention structure 102 is a mesh tubular shape formed from one or more braided or woven wires (e.g., Nitinol wires). Alternately, the mesh can be formed from laser cutting or etching a solid tubular structure. The proximal end of the retention structure 102 is fixed or mounted to a distal portion of the pusher 110 via welding, adhesive, a mechanical fixture, or any combinations of these methods.

Retention structure 102 may also include one or more engagement elements 106 fixed to its mesh 104 to assist the retention structure 102 in engaging the stent 1. The engagement elements 106 can take the form of polymeric or metallic protrusions that are one or more of the following shapes: spherical, elliptical, oval, pyramidal, rectangular, conical, truncated cone, truncated pyramid, square, or similar shapes. These engagement elements 106 can be attached via adhesive, wire or fiber ties, or welding, such that they protrude radially inwardly from the retention structure 102. The engagement elements 106 are sized and positioned on the mesh 104 so as to at least partially fit within gaps in the stent 1. For example, the engagement elements 106 may align with the end loops 4, minor loops 7, or the gaps formed between the woven wires of the stent 1. In this respect, when the retention structure 102 and stent 1 are radially compressed within the catheter 112 (or delivery sheath), the engagement elements 106 prevent the stent 1 from lateral or axial movement within the catheter 112, preventing the stent 1 from escaping until the retention structure 102 is exposed and radially expanded.

The retention structure 102 in FIG. 3 is illustrated with a trumpeted or conical distal portion which may be useful to ensure the stent 1 is locked down or engaged during delivery and deployment. Prior to connection to the pusher 110, the mesh 104 can be heat-set to form a radially-expanded tubular shape, so that once the proximal end of the mesh 104 is connected to the pusher 110, the mesh 104 expands to the conical shape. Alternately, the mesh 104 can be heat-set to form a trumpeted/conical shape prior to its connection to the pusher 110. In another alternate embodiment, the mesh 104 can be heat-set to form a conical shape having an abrupt inward taper at its distal end to act as a hook or circular ridge against the stent 1. In another alternate embodiment, the mesh 104 can form an undulating shape that increases and decreases in diameter along its length.

In the embodiment of the delivery system 100 of FIGS. 2-5, the pusher 110 can be an elongated member that is sufficiently flexible to advance through a patient's vascular system, while also maintaining sufficient pushability to push the retention structure 102 and stent 1 out of the catheter 112.

Referring to FIGS. 2-5, in operation, the distal end of the catheter 112 is advanced to a target treatment location (or adjacent that location) within a patient's vascular system. This positioning can be achieved by first advancing a guidewire so that the guidewire's distal end is located at or near the target treatment location. A delivery sheath can be advanced over the guidewire so that its distal end is located at the target treatment location, or the catheter 112 can advanced over the guidewire without the use of a delivery sheath. Several different techniques of positioning a catheter within the vasculature of a patient are known in the art and can be used with the embodiments of the present invention.

Once the distal end of the catheter 112 is located at a desired location, the pusher 110 is advanced distally. As seen in FIG. 4, a distal portion of the stent 1 is advanced out of the catheter 112 and begins to radially expand. As the stent 1 continues to advance distally, the retention structure 102 also advances distally out of the catheter 112, maintaining at least a portion of the proximal end of the stent 1 in a radially compressed (or partially compressed) configuration, despite being fully outside of the catheter 112.

If the distal portion of the stent 1 has not deployed to the desired target location in the vessel, the pusher 110 can be withdrawn proximally by the physician. As the retention structure 102 is withdrawn, it radially compresses, thereby compressing the proximal end of the stent 1 so as to allow it to reenter the lumen of the catheter 112. The engagement elements 106 help the retention structure 102 to grasp and pull the stent 1, ensuring that the stent 1 does not slip out of the retention structure 102. Once a portion of the stent 1 has reentered the catheter 112, the remaining portion of the stent 1 can also be withdrawn into the catheter 112, as well.

Finally, the catheter 112 is repositioned and the pusher 110 is advanced distally to deploy the stent 1 as previously described. Once the retention structure 102 has been sufficiently advanced out of the catheter 112, as seen in FIG. 5, it radially expands to a sufficient size so as to disengage with the stent 1. The pusher 110 and retention structure 102 are proximally withdrawn into the catheter 112 and the catheter 112 is withdrawn from the patient.

Figure 6:
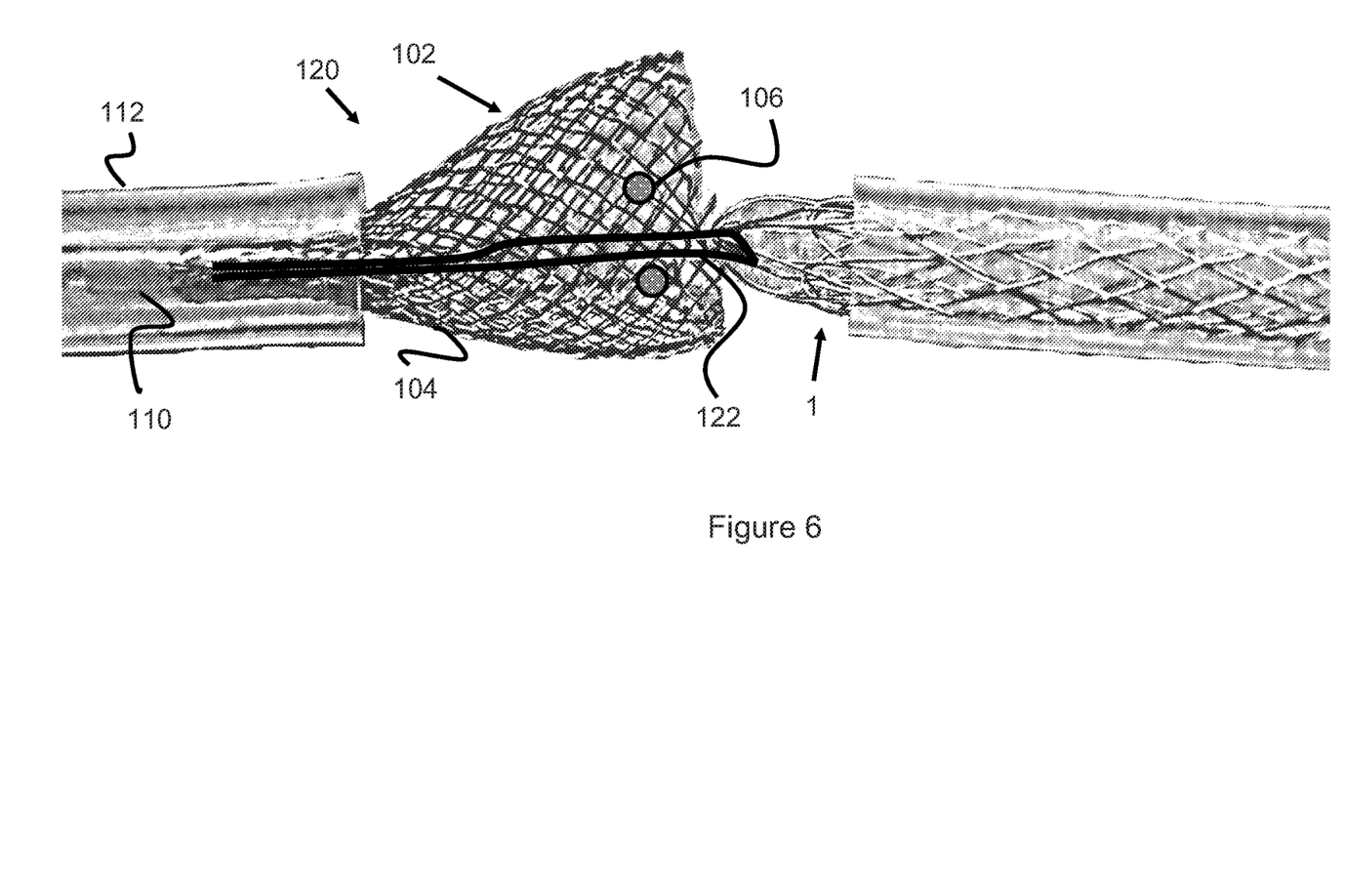
FIG. 6 illustrates a side view of another embodiment of a delivery system with a mesh or woven retaining structure and a tether.

FIG. 6 illustrates another embodiment of a delivery system 120 that is generally similar in structure and function to the delivery system 100 that has been previously described. However, the delivery system 120 further includes a tether 122 that is connected to the pusher 110 and can be selectively released from the stent 1 when fully deployed in a desired target location. The tether 122 can be a single filament that is fixed to both the pusher 110 and attached to the proximal loops of the stent 1 (e.g., via adhesive, mechanical ties, or welding). The tethering feature described in FIG. 6 (and alternatively in FIGS. 8 and 9) may be used in conjunction with the retention structure 102 or in lieu of the retention structure 102.

Figure 7:
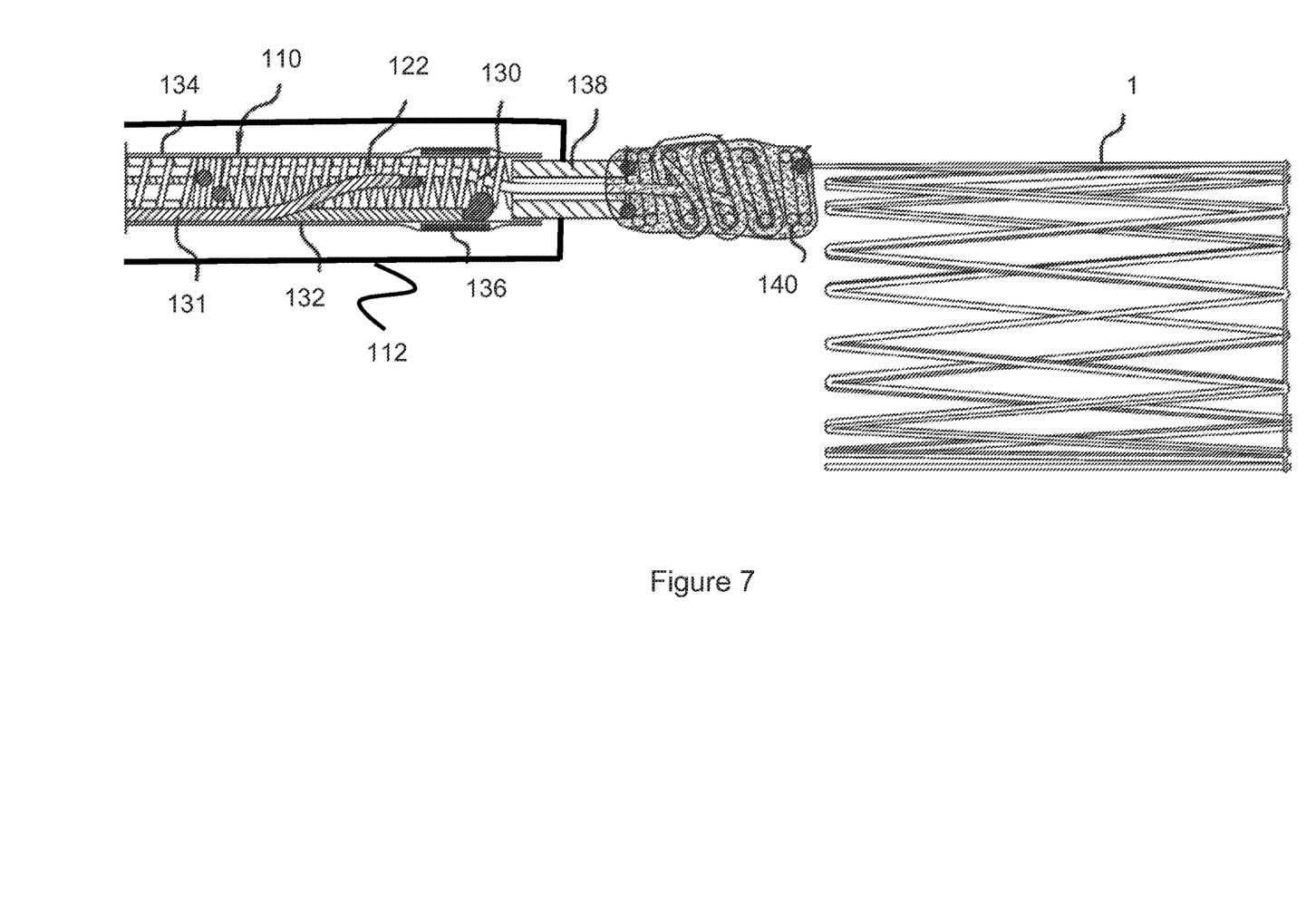
FIG. 7 illustrates a side view of a pusher that can be used with different embodiments of the present invention.

FIG. 7 illustrates an embodiment of a pusher 110 of FIG. 6, that illustrates the disconnect function. As seen in FIG. 7, the stent 1 is connected to the pusher 110 via a tether 122 and can be selectively activated to break the tether 122 to release the stent 1. More specifically, a resistance heater coil 130 is connected to electrical wires 131 and 132 that selectively supply power from a proximal power source. As the power is supplied, the heater coil 130 heats up, breaking the tether 122. An insulating cover 134 and reinforcement ring 136 are disposed on the outer portion of the pusher 110 to thermally isolate and reinforce the structure of the pusher 110.

In the embodiment of FIG. 7, the tether 122 extends through a proximally directed coil portion 138 and coil 140 of the stent 1, and is further adhered via adhesives 140. However, the tether 122 may also attach at both of its ends to the pusher 110, forming a loop around one or more of the end loops 4 of the stent 1.

Figure 8:
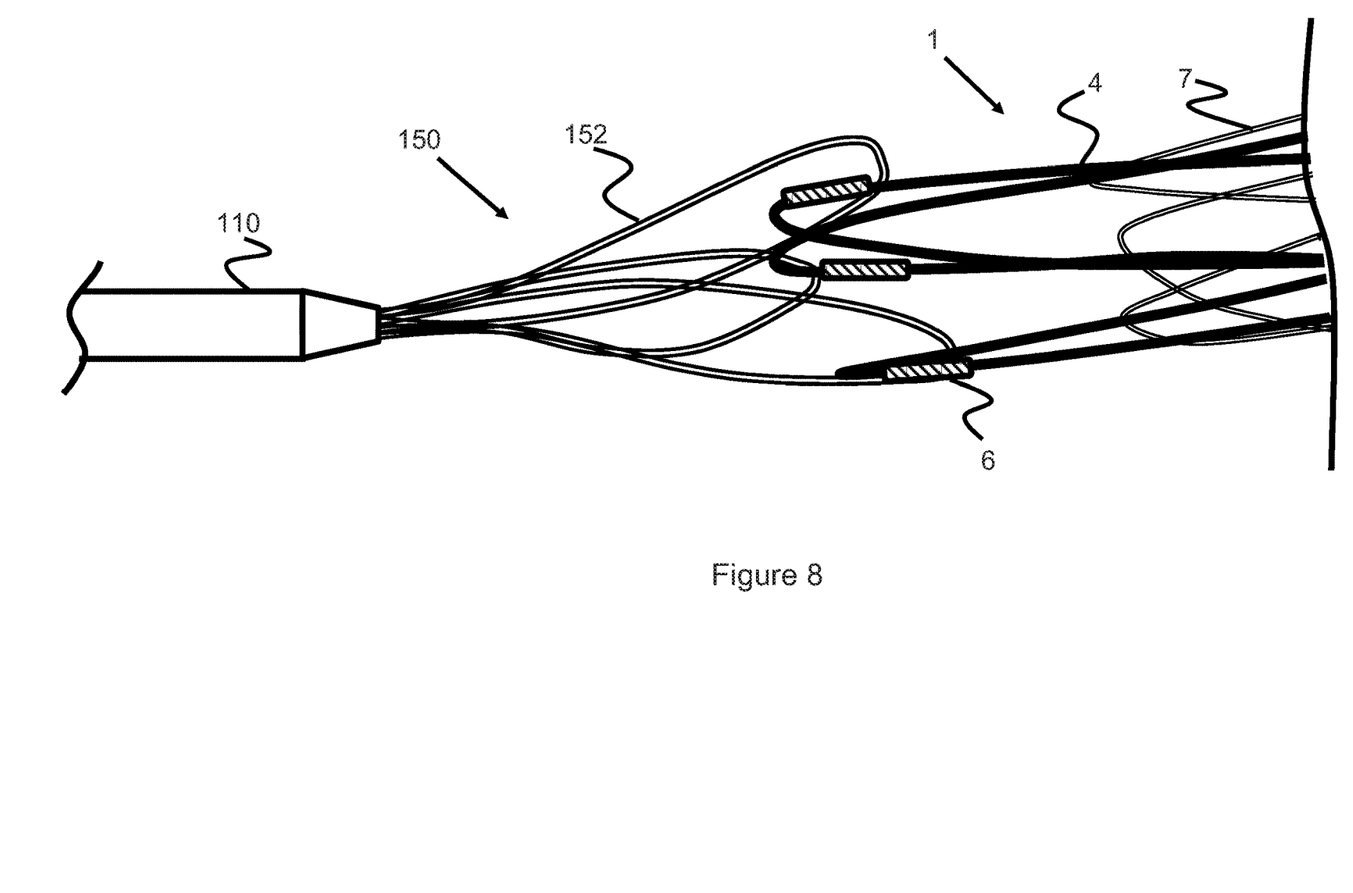
FIG. 8 illustrates a side view of another embodiment of a delivery system with a plurality of loops that comprise the retaining structure.

FIG. 8 illustrates another embodiment of a pusher 110 having a retention structure 150 composed of a plurality of loops 152. The loops 152 can press against an outer surface of each of the end loops 4 to help maintain the proximal portion of the stent 1 in a compressed configuration similar to that described for the retention structure 102. Alternately, each of the loops 152 can be positioned through each of the stent loops 4 or 7.

If the loops 152 are positioned on the outside of the stent loops 4 (i.e., not through the loops 4), the delivery method is similar to that of the delivery system 100 shown in FIGS. 4 and 5. If the loops 152 are positioned through the stent loops 4 (i.e., in a "chain-like" interlocking manner), the delivery method is similar to that of the delivery system 120 of FIG. 6, with regard to the detachment shown in FIG. 7.

While the retention structure 150 is illustrated with three loops 152, different numbers of loops 152 can be used, such as 2, 4, 5, 6, 7, 8, 9, or 10. In one embodiment, the number of loops 152 is equal to the number of stent loops 4 on the end of the stent 1. In another embodiment, one or more of the loops 152 can pass through more than one stent loop 4.

If the loops 152 are positioned on the outside of the stent loops 4 (i.e., not through the loops 4), they may be composed of a shape memory alloy. If the loops 152 are positioned through the stent loops 4 (i.e., in a "chain-like" interlocking manner), the loops 152 are preferably composed of a polymer that can be detached or broken by a mechanism in the pusher 110. For example, the pusher 110 may be that shown in FIG. 7 and therefore is configured to generate heat to break at least one strand or location along the loop 152.

Figure 9:
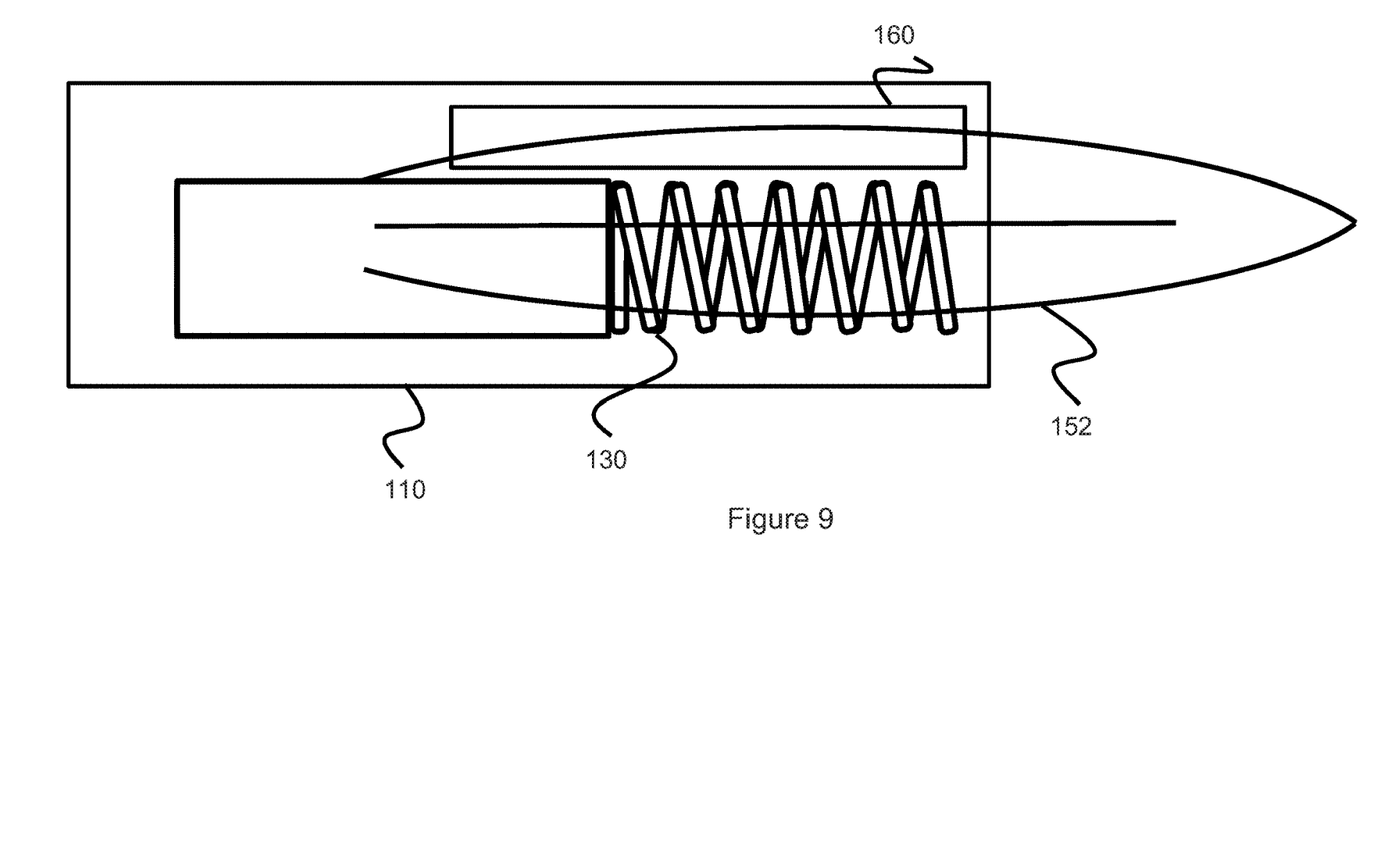
FIG. 9 illustrates a side view of a pusher and the looped retaining structure of FIG. 8.

As seen in FIG. 9, the loops 152 can also each have two free ends (i.e., is initially a linear configuration) that are both fixed internally to the pusher 110 or can initially be complete loop filaments in which a single location on the loop is fixed within the pusher 110. In the arrangement with two free ends (i.e., a linear strand), preferably only one end portion or section of each of the strand of the loops 152 passes through the heater coil 130 while a portion at the opposite end of the strand is positioned outside of the heater coil 130. The strand may also pass through an insulating sleeve 160 positioned adjacent the heater coil 130 to thermally isolate it from heat generated by the heater coil 130. In this respect, once the loop 152 is severed, the remaining portions of the strands of the loops 152 remain connected to the pusher 110 after breakage by the heater coil 130 and the stent loops 4 are released from the pusher 110.

Other embodiments of the pusher 110 utilize a multiple lumen structure in which the heater coil 130 and a first portion of the loop 152 are located within one inner lumen and a second portion of the loop 152 is located in a separate outer lumen. This separate lumen would prevent the second portion of loop 152 from having any contact with the heater coil 130.

Additional embodiments may utilize multiple loop structures, such as one delivery loop 152 which grasps all the stent loops 4 as well as separate, individual delivery loops 152 which grasp only one stent loop 4. Additional variations may use fewer delivery loops 152 than the total number of stent loops 4 provided. Thus, for example, three stent-loops 4 are used with two delivery loops 152. In another example, one delivery loop 152 engages two stent loops 4 and the other delivery loop 152 engages only one stent loop. Additional embodiments may use multiple loop structures 152 for each stent loop 4 (e.g., two delivery loops 152 to snare each stent loop 4) in order to further augment retention. Variations are also possible in which combinations of each of the various embodiments described are used (e.g., some stent loops 4 utilize multiple delivery loops 152, some stent loops 4 utilize only one delivery loop 152, and some delivery loops 152 grasp multiple stent loops 4).

It should be understood that elements or aspects from the various embodiments presented herein can be combined in a wide array of different configurations. For example, one embodiment may utilize a combination of a mesh retention structure 102, a delivery loop retention structure 150, and a tether 122 to further enhance the retention capabilities of the implant delivery system.

The presence of one or more tethers 122 may not necessarily prevent the expansion of the stent 1 after exiting the catheter 112, since stents 1 generally have a strong shape memory and quickly adopt their expanded state upon delivery. However, if the tether 122 was in sufficiently high tension, the tensile force of the tether 122 may keep the proximal portion of the stent 1 from expanding, and thus keep the stent 1 connected to the retention structure 102. A spring, coil, or tube can be used to keep the tether 122 in a tensioned state to further augment the tensile force of the tether 122.

With regard to embodiments utilizing one or more tethers 122, delaying the tether 122 detachment until after the stent 1 has fully expanded may allow the stent 1 to be repositionable while the tether(s) 122 are attached, since the tether(s) 122 connect the stent 1 to the delivery pusher 110 (some additional variables might still impact repositionability such as the size/weight of the stent 1 and the narrowness of the vessel). Once the retention structures 102 and tethers 122 are detached, the stent 1 is detached from the pusher 110 entirely and is likely not repositionable after this point.

The delivery system embodiments described can be used to deliver one or more implants such as stents, stent grafts, embolic coils, occluders, plugs, and similar devices. While the example of a stent was described in the embodiments of this specification, any of these other implants may similarly be used. For example, to deliver an embolic coil, the mesh retention structure 102 supports the proximal portion of an embolic coil for releasable delivery. The proximal part of an embolic coil may have a receiving structure to accommodate the engagement elements 106 of the retention structure 102. Other implants may also include a loop structure 4 at a proximal region of those implants.

Any figures shown and/or described are not meant to be limited exclusively to the representation of what is shown and instead are illustrative in nature. Similarly, any measurements and/or descriptions of materials are meant to be representations, approximations, and examples rather than being expressly limiting.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A delivery system for an implant, comprising:
   an elongated pusher having a distal pusher end and a proximal pusher end;
   a retention structure having a proximal structure end fixed to said pusher near said distal pusher end, and a distal structural end being located distally away from said distal pusher end; said retention structure having a radially compressed configuration and a radially expanded configuration;
   a plurality of engagement elements fixed on said retention structure and protruding radially inwards of said retention structure; and,
   an implant located near said distal pusher end and in contact with said retention structure;
   wherein said distal structural end of said retention structure is positioned over a proximal end of said implant so as to leave a distal end of said implant uncovered by said retention structure; and,
   wherein said retention structure engages said implant in said radially compressed configuration and releases said implant in said radially expanded configuration.

2. The delivery system of claim 1, wherein said retention structure is composed of mesh formed from one or more braided wires.

3. The delivery system of claim 2, wherein said retention structure has a tubular shape in said radially compressed configuration and a conical shape opening distally relative to said elongated pusher when in said radially expanded configuration.

4. The delivery system of claim 3, wherein said implant is a stent having a plurality of loops extending from its proximal end.

5. The delivery system of claim 4, wherein said retention structure overlaps a proximal portion of said stent.

6. The delivery system of claim 1, wherein the implant includes a plurality of gaps sized to fit the plurality of engagement elements.

7. The delivery system of claim 6, wherein the implant is comprised of braided wires, a plurality of braided wire crossing points, and the gaps of the implant are located between braided wire crossing points of the implant.

8. A delivery system for an implant, comprising:
   a catheter having a passage therethrough between a distal catheter end and a proximal catheter end;
   an elongated pusher having a distal pusher end and a proximal pusher end; said elongated pusher being disposed in said passage of said catheter so as to move longitudinally relative to said catheter;
   a retention structure having a proximal structure end fixed to said pusher near said distal pusher end, and a distal structural end being located distally away from said distal pusher end; said retention structure having a radially compressed configuration and a radially expanded configuration; said retention structure including a plurality of engagement structures connected to and protruding from said retention structure; and,
   an implant located near said distal pusher end and in contact with said retention structure;
   wherein said distal structural end of said retention structure is positioned over a proximal end of said implant while leaving a distal end of said implant exposed by said retention structure; and,
   wherein said retention structure engages said implant in said radially compressed configuration within said passage of said catheter and releases said implant in said radially expanded configuration when advanced distally outside of said distal catheter end.

9. The delivery system of claim 8, wherein said retention structure is composed of mesh formed from one or more braided wires; and wherein said retention structure has a tubular shape in said radially compressed configuration and a conical shape opening distally relative to said elongated pusher when in said radially expanded configuration.

10. The delivery system of claim 8, wherein said engagement structures are composed of a polymer or metal; and wherein said engagement structures are spherical, elliptical, oval, pyramidal, rectangular, conical, truncated cone, truncated pyramid, or square.

11. The delivery system of claim 8, wherein the implant includes a plurality of gaps sized to fit the plurality of engagement elements.

12. The delivery system of claim 11, wherein the implant is comprised of braided wires, a plurality of braided wire crossing points, and the gaps of the implant are located between braided wire crossing points of the implant.

13. A vessel prosthesis delivery device comprising:
an elongated pusher having a distal pusher end and a proximal pusher end;
a retention structure connected to the pusher, the retention structure comprising a mesh of braided wires;
the retention structure having a proximal end fixed to the pusher near the distal pusher end, and a distal end of the retention structure being free from direct connection to the pusher so as to allow radial expansion of the distal end of the retention structure and being at least partially located distally of the distal end of the pusher, the retention structure having a radially compressed configuration and a radially expanded configuration; and,
engagement elements protruding radially inward of the retention structure and sized to fit corresponding gaps in a prosthesis.

14. The vessel prosthesis delivery device of claim 13, wherein the retention structure has a conical or trumpeted shape.

15. The vessel prosthesis delivery device of claim 13, wherein the shape of the engagement elements is spherical, elliptical, oval, pyramidal, rectangular, conical, truncated cone, truncated pyramid, or square.

16. The vessel prosthesis delivery device of claim 13, wherein the prosthesis is comprised of braided wires, a plurality of braided wire crossing points, and the gaps of the prosthesis are located between braided wire crossing points of the prosthesis.

17. The vessel prosthesis delivery device of claim 13, wherein the prosthesis has proximal end loops and the gaps of the prosthesis gripped by the engagement elements are located at the proximal looped end of the prosthesis.

18. The vessel prosthesis delivery device of claim 13, wherein the retention structure has a plurality of braided wire crossing points, and wherein there are a plurality of retention structure gaps located between the plurality of braided wire crossing points, and the engagement elements are located in the retention structure gaps.

19. The vessel prosthesis delivery device of claim 13, wherein the retention structure is heat set to adopt a radially compressed configuration when constrained within a delivery sheath and a radially expanded configuration when not constrained within a delivery sheath.

20. The vessel prosthesis delivery device of claim 13, wherein the distal end of the retention member extends distally beyond the distal end of the pusher.

* * * * *